United States Patent
Popescu

(10) Patent No.: US 11,454,686 B2
(45) Date of Patent: Sep. 27, 2022

(54) GRADIENT SYSTEM FOR A MAGNETIC RESONANCE IMAGING SYSTEM

(71) Applicant: Siemens Healthcare GmbH, Erlangen (DE)

(72) Inventor: Stefan Popescu, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 17/101,197

(22) Filed: Nov. 23, 2020

(65) Prior Publication Data

US 2021/0156937 A1 May 27, 2021

(30) Foreign Application Priority Data

Nov. 27, 2019 (EP) .................................. 19211922

(51) Int. Cl.
*G01R 33/385* (2006.01)
*G01R 33/381* (2006.01)
*G01R 33/48* (2006.01)
*G01R 33/34* (2006.01)

(52) U.S. Cl.
CPC ......... *G01R 33/385* (2013.01); *G01R 33/381* (2013.01); *G01R 33/4816* (2013.01); *G01R 33/34061* (2013.01)

(58) Field of Classification Search
CPC ............... G01R 33/385; G01R 33/381; G01R 33/4816; G01R 33/34061
See application file for complete search history.

(56) References Cited

U.S. PATENT DOCUMENTS

| 4,644,275 | A | * | 2/1987 | Young | G01R 33/381 324/307 |
| 4,668,915 | A | * | 5/1987 | Daubin | G01R 33/28 324/309 |
| 5,490,513 | A | * | 2/1996 | Damadian | G01R 33/341 600/415 |
| 5,606,970 | A | * | 3/1997 | Damadian | G01R 33/381 600/415 |
| 5,623,927 | A | * | 4/1997 | Damadian | G01R 33/341 600/415 |

(Continued)

FOREIGN PATENT DOCUMENTS

| EP | 3736590 A1 | 11/2020 |
| EP | 3736591 A1 | 11/2020 |

(Continued)

OTHER PUBLICATIONS

Matsuda et al., "Super-Parallel MR Microscope," Magnetic Resonance in Medicine, vol. 50, pp. 183-189 (2003).

(Continued)

*Primary Examiner* — Dixomara Vargas
(74) *Attorney, Agent, or Firm* — Banner & Witcoff Ltd.

(57) ABSTRACT

A gradient system for a magnetic resonance imaging system can include at least two examination areas using a common basic magnetic field and a number of gradient coils in the at least two examination areas, and a gradient controller configured such that it controls the electric current flowing through at least two gradient coils for similar gradient axes in different examination areas in a temporal synchronous manner.

14 Claims, 8 Drawing Sheets

(56) References Cited

U.S. PATENT DOCUMENTS

| | | | |
|---|---|---|---|
| 5,664,569 A * | 9/1997 | Damadian | G01R 33/341 |
| | | | 600/421 |
| 5,793,209 A | 8/1998 | Kondo et al. | |
| 7,880,467 B2 * | 2/2011 | Rapoport | G01N 24/085 |
| | | | 324/309 |
| 11,209,513 B2 * | 12/2021 | Popescu | G01R 33/543 |
| 2002/0030491 A1 | 3/2002 | Kose | |
| 2005/0258832 A1 * | 11/2005 | Eberlein | G01R 33/385 |
| | | | 324/318 |
| 2006/0279281 A1 * | 12/2006 | Rapoport | G01N 24/085 |
| | | | 324/308 |
| 2010/0102815 A1 | 4/2010 | Parker et al. | |
| 2016/0238681 A1 * | 8/2016 | Biber | G01R 33/3852 |
| 2020/0355764 A1 * | 11/2020 | Popescu | G01R 33/34007 |
| 2020/0355771 A1 * | 11/2020 | Popescu | G01R 33/481 |
| 2021/0156936 A1 * | 5/2021 | Popescu | A61B 5/4547 |
| 2021/0156941 A1 | 5/2021 | Popescu et al. | |

FOREIGN PATENT DOCUMENTS

| | | |
|---|---|---|
| EP | 3828573 A1 | 6/2021 |
| EP | 3828580 A1 | 6/2021 |
| JP | H10234704 A | 9/1998 |

OTHER PUBLICATIONS

Littin et al., "Development and Implementation of an 84-Channel Matrix Gradient Coil," Magnetic Resonance in Medicine, vol. 79, No. 2, pp. 1181-1191 (2018).

EP Search Report for EP Application No. 19211922.0, dated Jun. 26, 2020.

* cited by examiner

FIG 6
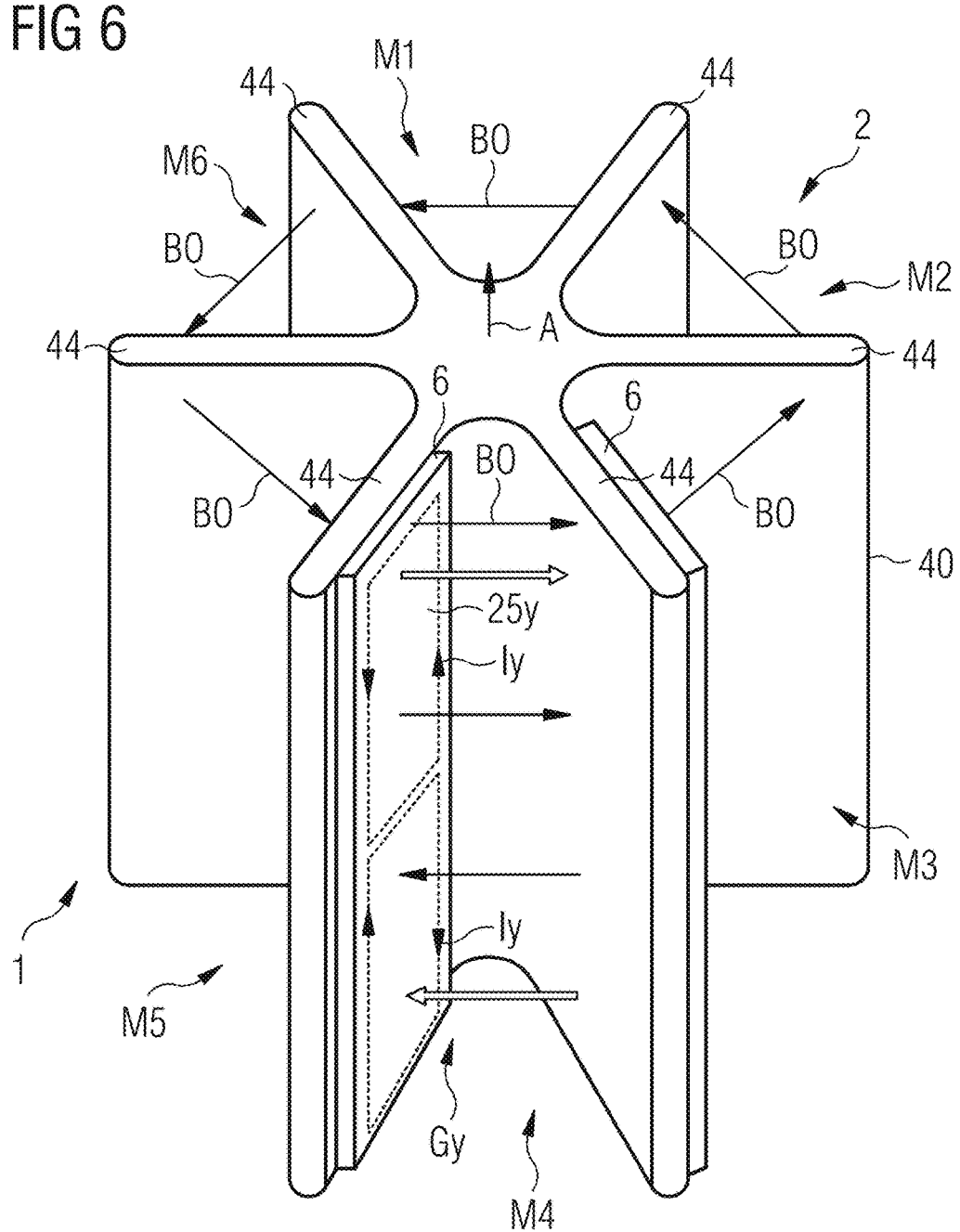
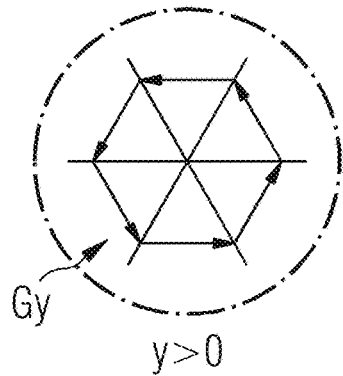
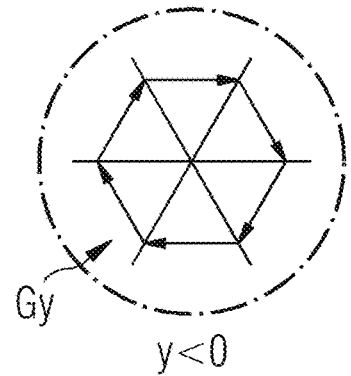

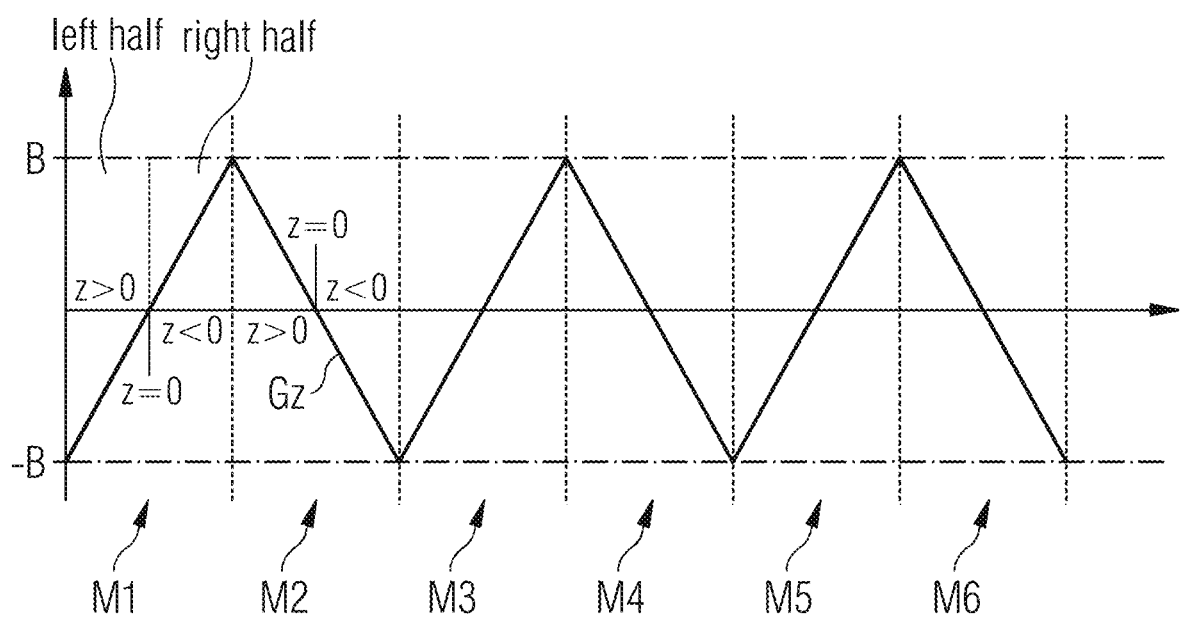

GRADIENT SYSTEM FOR A MAGNETIC RESONANCE IMAGING SYSTEM

CROSS REFERENCE TO RELATED APPLICATIONS

This patent application claims priority to European Patent Application No. 19211922.0, filed Nov. 27, 2019, which is incorporated herein by reference in its entirety.

BACKGROUND

Field

The disclosure describes a gradient system for a magnetic resonance imaging system ("MRI-system"), especially for a MRI-system with two or more examination areas, and such MRI-System. The disclosure further describes a method to control such gradient system, a controller for an MRI-system and such magnetic resonance imaging system.

Related Art

For more than four decades, the principle of magnetic resonance imaging ("MRI") has been used for imaging and other measurements. Despite this long time and the importance of this method of measurement, only two magnet designs are currently used for MRI systems or MRI scanners in clinical use: C-magnet forms and solenoids. Operation of this type of MRI scanner still are problematic for the clinical workflow.

The most serious problems occur with regard to the extensive stray magnetic fields around these scanners. In order to cope with this problem and avoid accidents and damage, the hospital administration must delineate a strictly controlled area within and in the vicinity of the MRI examination rooms by limiting the access of people and equipment. Damage can occur if metallic or magnetic parts are attracted by the strong magnets of the MRI scanner and accelerated in the direction of the scanner volume.

Another problem is that the MRI scanners, which use a solenoid-magnet design, "enclose" patients in a narrow patient tunnel, which in particular can cause claustrophobia. This claustrophobia may be so strong in some patients that no MRI scan can be performed. Moreover, due to the narrowness of the examination tunnel, the access of the medical staff to the patient is severely restricted, which is unfavorable for interventional or therapeutic procedures, in particular with regard to real-time MRI imaging.

Typically, MRI scanners use a self-shielded, solenoid-type superconducting magnet to reduce the strength of the leakage magnetic field resulting from the coil of the basic field magnet. An actively shielded basic field magnet is much more expensive than an unshielded one. In addition, the shield coils reduce the efficiency of the basic magnetic field that can be used for measurements in an examination tunnel. Active shielded magnets have a larger diameter (about 220 cm) than unshielded magnets (about 145 cm).

Alternative designs for MR scanners use a C-shaped magnet. This can be either a permanent magnet or an electromagnet consisting of two Helmholtz coils. The C-shaped magnets have two magnetic pole pieces which create a vertical basic magnetic field in their space. An analogous structure is a portal magnet, which is mechanically more robust, and in some embodiments can also be realized with superconducting Helmholtz coils. The C-shape and the portal magnets have the advantage of open access to the patient and additionally reduce claustrophobic feelings. However, such a structure requires a very robust mechanical construction to counteract the enormous magnetic attraction force between the two opposed basic field magnets. To reduce the spread of stray magnetic fields, these magnet architectures typically use an iron yoke to guide and close the magnetic field lines outside the imaging volume. The iron yoke is one of the most cost-effective shields. The disadvantage of such a yoke is the big size, weight and volume of the MR scanner.

One approach to solve these problems has been introduced a short time ago. This approach is based on an MRI system with a toroidal magnetic field. Unlike the prior art of MR magnets that use solenoid or Helmholtz-pair magnet coils, the toroid coils tend to confine the magnetic field inside a torus with only a small and not so far reaching stray magnetic field. This system not only overcomes the problems of stray magnetic field and a light-weight construction, it also offers the opportunity to realize two or more examination areas in one single MRI-system. An example for such MRI-system is a basic field magnet arrangement with three, four, six or eight (e.g. identical) basic field magnet segments arranged in a star shape about a central axis with a rotational symmetry (e.g. 60° for six magnets and six examination areas). The basic magnetic field has a main direction which runs in the form of a toroidal magnetic field.

Another approach to solve these problems has also been introduced a short time ago. This alternative approach is based on a conventional MRI-scanner that is surrounded by "satellite scanners" that use the stray basic magnetic field of the conventional MRI-scanner. The additional scanners are surely not using a magnetic basic field as strong as inside the conventional MRI-scanner, however, they offer the opportunity to realize a number of non-expensive examination areas where basic examinations can be made. For example in cases of catastrophes or in secluded regions, one single (mobile) MRT system could be used for examining many patients simultaneously.

There are local gradient systems with coil pairs arranged parallel left and right of a patient. However, although such known gradient systems can also be used for these new MRI-systems, there is currently no gradient system working in an optimal way together with these MRI-systems. Especially, conventional gradient systems produce a stray field outside a conventional MRI-scanner that may affect the other examination areas of the above mentioned new MRI-systems.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

FIG. 6 shows an exemplary y-gradient field according to an exemplary embodiment of the disclosure.

FIG. 8 shows an exemplary z-gradient field in a graph according to an exemplary embodiment of the disclosure.

Figure 1:
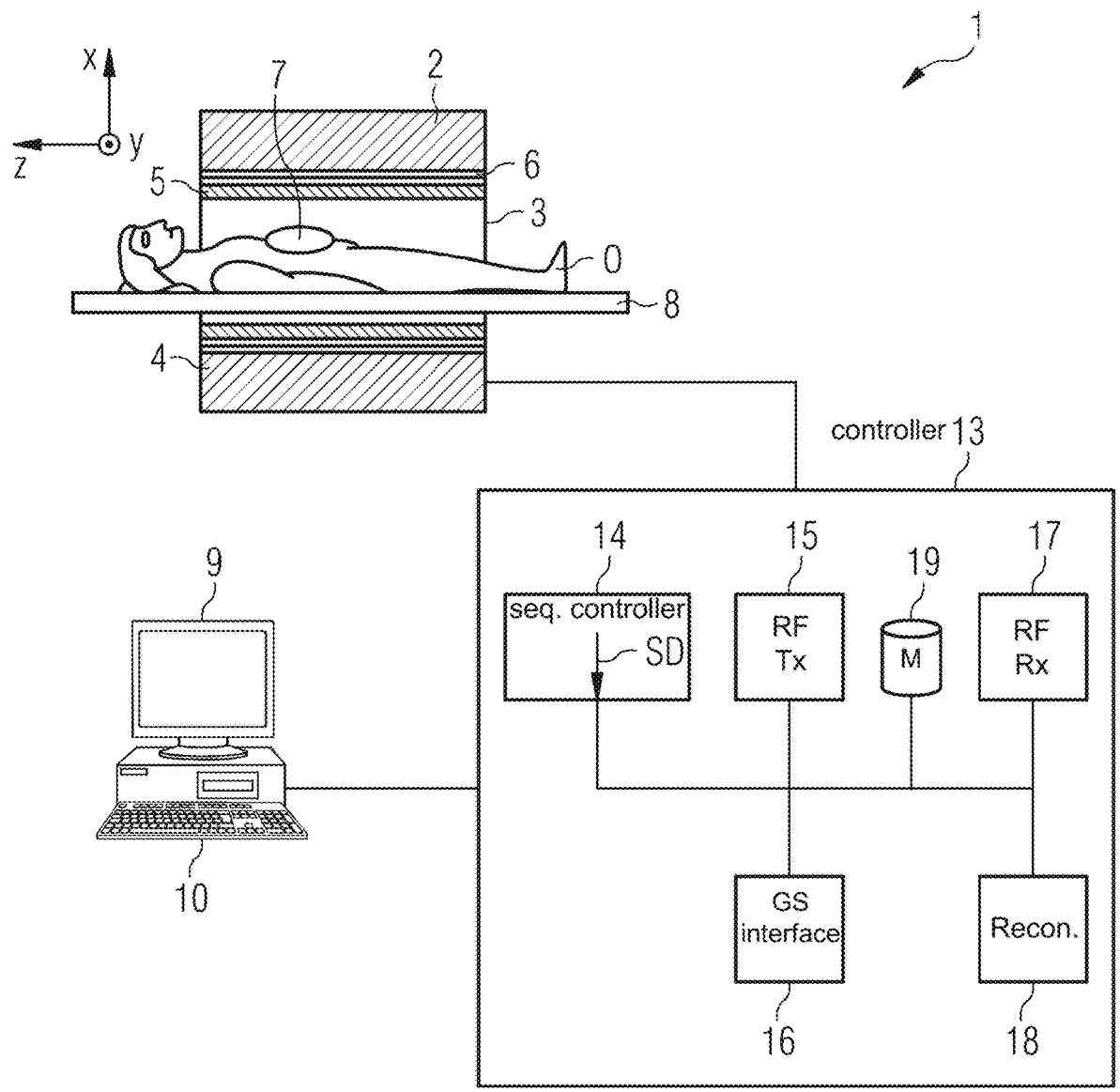
FIG. 1 shows a magnetic resonance imaging (MRI) system according to an exemplary embodiment of the disclosure.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

An object of the present disclosure is to improve the known MRI-systems to facilitate an improved gradient system suitable for MRI-systems with two or more examination areas, especially for producing spatially non-constant magnetic fields.

A gradient system according to the disclosure for a magnetic resonance imaging system includes at least two examination areas using a common basic magnetic field and a number of gradient coils. The gradient coils are arranged in at least two examination areas. The system additionally comprises a gradient controller configured such that it controls the electric current flowing through at least two gradient coils for similar gradient axes in different examination areas in a temporal synchronous manner.

A gradient system typically comprises gradient coils arranged in an examination area, e.g. at the basic field magnets confining an examination area. Although well-known gradient coils can be used, a special shape and/or a special arrangement can offer additional advantages, as described further below. Although the coils may comprise many different loops of a wire, all wire-loops on one side of an examination area that produce a gradient on the same axis are regarded as one single coil in the following.

The gradient controller may be a component providing control signals for a current for the gradient coils (e.g. as a controller for power amplifiers) as well as a unit providing the current itself (e.g. in the case the gradient controller comprises the respective power amplifier). The gradient controller is configured such that it controls the electric current flowing through at least two gradient coils in a temporal synchronous manner, i.e. at the same time. In an exemplary embodiment, a gradient controller is configured to coordinate all gradient activities, preferably the independent or synchronized operation of different gradient axes, especially even the minimization and/or the correction of cross-interference terms between the gradient coils.

Regarding gradient axes in different examination areas, it should be noted that the gradient axes follow local coordinate systems in the individual examination areas. Typically, the z-gradient axis follows the basic magnetic field. In a toroidal arrangement, the z-axes (all together) will run in a circle or a polygon, since the orientation of the basic magnetic field is different in every examination area and it has the shape of a circle or polygon. Similarly, the X-axis, typically pointing perpendicular to the basic magnetic field, parallel to the plane of the toroidal shape, will differ in every examination area, always pointing to the outside in the plane of the toroidal basic magnetic field. The y-axis typically points perpendicular to the basic magnetic field and its toroidal plane. In an exemplary embodiment, for each examination area there is a local coordinate system XYZ associated therewith, wherein the local Z-axis is running parallel to and pointing in the same direction with the static basic magnetic field B0, the Y-axis is parallel to the vertical rotational symmetry axis of the MRI-scanner, while the X-axis corresponds to the radial direction pointing from the center of symmetry outwards from the magnet through the vertical midplane of the imaging compartment.

Coils for similar gradient axes are both Z-gradient coils in the two examination areas or both X-gradient coils or both Y-gradient coils. The axes do not have to point in similar directions, they have to be the same axes concerning the local coordinate systems of the gradient coils in the individual examination areas.

A further global coordinate system may be connected to the whole MRI-scanner. In an exemplary embodiment, the global coordinate system includes a vertical Y-axis (the same as the rotational symmetry axis), a radial R-coordinate pointing from the symmetry axis radially outwards and an angular Θ-coordinate. For a star shaped arrangement of the basic field magnets of a MRT-scanner, the spatial relations between the global and the local coordinate systems are as follows: the local Y-coordinates are always equal to the global Y-coordinate. A local X-axis corresponds to a radial spoke going through the vertical midplane of an imaging compartment. All the local Z-axes together combine to build up the sides of a polygon cutting through the horizontal midplane of the magnet and centered around the symmetry axis.

Surely, the gradient system should also comprise further components that the gradient systems of the state of the art also comprise for an optimal operation. These are e.g. dedicated gradient power amplifiers for each axis GPAx, GPAy and GPAz, shim coils or holding structures.

Such gradient system has the advantage that it produces a special, synchronized gradient field. It is very advantageous for MRI-scanners with inclined arrangements of basic field magnets as e.g. star-shaped arrangements. It is also advantageous for above mentioned "satellite scanners".

A method according to the disclosure, especially to control a gradient system according to the disclosure, to apply a gradient field for at least two examination areas with gradient coils, comprises the step:

applying an electric current flowing through at least two gradient coils for similar gradient axes in different examination areas in a temporal synchronous manner.

Thus, there are at least two gradient fields applied in two different examination areas on similar axes (either X or Y or Z axis) at the same time. Surely, the method can be applied to more than one axis, so that two axes or all three axes are driven synchronically, wherein the synchronous operation is essential for any similar axes.

A controller according to the disclosure for a magnetic resonance imaging system is configured to apply an electric current flowing through at least two gradient coils for similar gradient axes in different examination areas in a temporal synchronous manner. In an exemplary embodiment, the controller includes a system according to the disclosure. The controller may comprise additional units or devices for controlling components of a magnetic resonance imaging system, e.g. a sequence controller for measurement sequence control, a memory, a radio-frequency transmitter that generates, amplifies and transmits RF pulses, a gradient system interface, a radio-frequency receiver to acquire magnetic resonance signals and/or a reconstructor to reconstruct magnetic resonance image data.

A magnetic resonance imaging system comprises at least two examination areas, and a gradient system according to the disclosure and/or a controller according to the disclosure. A MRI-scanner, according to an exemplary embodiment, of such magnetic resonance imaging system comprises a inclined arrangement of basic field magnets, e.g. a star-shaped arrangement. MRI scanners with a toroidal MRI-scanner architecture are particularly preferred. In a star shaped arrangement of basic field magnets with a toroidal magnetic field, the front side of the gradient system should point to the outside of the toroid magnetic field.

In an exemplary embodiment, a gradient system comprises a group of gradient coils for a similar gradient axis in different examination areas (all for X-, all for Y- or all for Z-axis in the examination areas), wherein the gradient coils of the group are electrically connected in a series and/or parallel connection, and the group being powered by a (especially one single) power unit, e.g. a power amplifier of the gradient controller. In an exemplary embodiment, the gradient coils for a similar gradient axis in all examination areas (all X-, all Y- or all Z-coils) are powered by this principle (one single power unit per axis). This has the advantage that an easy synchronized operation can be realized. A series connection has the further advantage that the current in all coils connected in series is the same.

To clarify the position in a 3D coordinate system, there is a reference to a central plane of the gradient coils. The central plane of a coil is the plane of the loops of the coil (or at least an averaged middle plane). Looking at a planar gradient coil, the central plane is the plane of the coil, looking at a Helmholtz coil, the central plane is the plane of the windings of the coil, wherein the gradient magnetic field vector is perpendicular to the central plane. In an exemplary embodiment, the gradient coils (i.e. the X, Y, and/or Z gradient coils) are arranged at opposite walls of an examination area. The examination area of a gradient system is the area between the gradient coils, since at normal use in an MRT scanner, the examination area for the MRI examination would be between the gradient coils.

In a gradient system according to an exemplary embodiment, the gradient coils comprise a central plane and are arranged such that the central planes of two adjacent gradient coils are at an angle greater than 10° to another so that the gradient system is V-shaped. This arrangement is advantageous for star shaped MRI-scanner arrangements. For better understanding it is defined here that the "front side" of the gradient system is the mouth of the V-shape and the "back side" is the opposite side, where the gradient coils of a pair are nearest to each other. The vector of the X-Axis points to the front side of the gradient system.

In a gradient system according to an exemplary embodiment, the gradient coils are arranged such that a resulting gradient field has a toroidal shape or a toroidal shape with straight passages (in the following called "toroidal arrangement"), wherein the gradient coils are arranged star-shaped around at least one central axis, especially rotary-symmetrical. The special arrangement of the coils tend to confine the magnetic field inside the torus with only a small and not so far reaching stray magnetic field. Thus, there is no need for an expensive magnetic shield.

Typically, gradient coils are arranged at opposite sides of an examination area as a pair so that there is a coil for a gradient axis at one side and one coil for this axis on the other side of an examination area. This means that there are two gradient coils for each gradient axis in each examination area. Typically, the gradient system creates gradients in X, Y and Z direction to realize a gradient vector with X, Y and Z contributions. In an exemplary embodiment, there is a pair of X-gradient coils, a pair of Y-gradient coils and a pair of Z-gradient coils. It is clear that two gradient coils configured to create the same gradient (and being arranged on different sides of an examination area) are forming a pair.

Unlike the prior art it is not required to provide a pair of gradient coils for each gradient axis in each imaging compartment. Especially with the described toroidal arrangement one gradient coil for a gradient axis could serve for two adjacent examination areas so that there is not the need for pairs of gradient coils. For example in a MRI-scanner with six examination areas and a toroidal basic magnetic field, it is sufficient to provide a minimum of six gradient coils for each axis, which means that each imaging compartment (i.e. examination area) hosts a single gradient coil for the X-axis, a single gradient coil for the Y-axis and a single gradient coil for the Z-axis.

In a gradient system according to an exemplary embodiment, gradient coils are arranged such that an examination area comprises a single gradient coil for a gradient axis (on one single side), only. This means that there is only one gradient coil for the X-axis, one gradient coil for the Y-axis and one gradient coil for the Z-axis in one examination area. This coil is especially arranged on the "wall" (basic field magnet) between two adjacent examination areas. In an exemplary embodiment, the number of gradient coils for a group of examination areas corresponds to the number of examination areas in this group. This means that there are no pairs of gradient coils in this group. In an exemplary embodiment, a separating element between adjacent examination areas comprises only one gradient coil for each gradient axis for both examination areas.

In an exemplary embodiment, a system of planar gradient coils realized as planar solenoids collaborate to generate the gradient field over all imaging volumes. This collaboration is not only based on the synchronized operation, but also based on the arrangement of the coils.

Accordingly, it is not required to have two gradient coils enclosure units in each examination area. In some particular embodiments and in order to save space it may be sufficient to foreseen only a single enclosure, that is either only on the one side (e.g. the left-hand part) or only the other side (e.g. the right-hand part) is available within an imaging compartment. Surely, special combinations are possible without limiting the scope of this disclosure. For example, the one side (e.g. the left-hand part) may host two gradient coils for two different axes (e.g. the X and Y gradient coils), whereas the other side (e.g. the right-hand part) hosts only one gradient coil for one axis (e.g. the Z gradient coil).

In a gradient system according to an exemplary embodiment, the gradient coils are bi-planar gradient coils. This has the advantage that the gradient system does not need much space. In an exemplary embodiment, the central planes of gradient coils on one side of the examination area are parallel to each other, especially in the case the gradient coils are bi-planar gradient coils.

In an exemplary embodiment, the gradient system comprises two or three pairs of gradient coils (e.g. X, Y and Z gradient coils), wherein all pairs of gradient coils are arranged in the same angle to another, i.e. the angle between the central planes are equal.

In an exemplary embodiment, a number of gradient coils is formed to cover a side of a whole field-of-view (FoV), or at least a part of the FoV, of an examination area, preferably being mechanically and/or permanently attachable to an MRI-scanner. In an exemplary embodiment, the gradient coil system has two building blocks symmetrically (mirror symmetry or rotational symmetry) located at the right side (say block 1) and the left side (say block 2) of the examination area. The right block 1 and the left block 2 are preferably mirrored paired or rotationally paired. In an exemplary embodiment, each block integrates at least one gradient coil for one axis. Generally, each block integrates three gradient coils for all three axes. This means that the block 1 comprises a stack of planar gradient coils, e.g. the right half of the X, Y and Z gradient coils. Especially with a V-shaped basic-magnet arrangement, an (or each) examination area has a V-shaped gradient coil system attached to the basic field magnets and comprising the two blocks. Such V-shaped architecture of gradient coils makes better use of the mounting space available within the examination regions that is shaped like a triangular or trapezoidal prism. As for the local gradients system, each block (1, 2) consists of a stack of planar gradient coils, e.g. each block integrates one half of the X, Y and Z gradient coil pairs.

It should be noted that a number of gradient coils could also be formed as local gradient coils, such as local gradient coils for head imaging. In an exemplary embodiment, the gradient coils are integrated into and/or are mechanically attached to the headrest of a patient chair.

A gradient system according to an exemplary embodiment includes magnetic field shim coils and/or active shielding coils, where these coils are arranged similar to the gradient coils (e.g. the central plane of these coils is parallel to the central plane of the gradient coils).

Regarding the above example, the gradient system blocks (1,2) could further integrate magnetic field shim coils and/or active shielding coils so configured to attenuate the stray gradient fields outside the imaging volume that would otherwise penetrate the adjacent examination regions and/or imaging volumes.

In a gradient system according to an exemplary embodiment, the gradient coils for the gradient of the Z-axis are connected such to the gradient controller that adjacent coils are applying a mirrored magnetic field.

It should be noted that in the case of the coils and the examination areas "adjacent" means in regard to the basic magnetic field. Thus, the predefined direction of the basic magnetic field defines the order of adjacent elements.

In a gradient system according to an exemplary embodiment, a gradient coil is formed by a plurality of loops of a conductor, where:

the loops of a gradient coil for the X-gradient comprises two sets of contra-rotating loops adjacent in X-direction, wherein the radius of a set of loops increases, with the outer conductors in X-direction essentially remaining at the sides of the gradient coil, the loops of a gradient coil for the Y-gradient comprising two sets of contra-rotating loops adjacent in Y-direction, wherein the radius of a set of loops increases, with the outer conductors in Y-direction essentially remaining at the sides of the gradient coil, the loops of a gradient coil for the Z-gradient comprising a set of increasing loops, wherein the center of the loops essentially remain in the center of the gradient coil.

In a gradient system according to an exemplary embodiment, regarding the gradient coil for the X-gradient and/or the gradient coil for the Z-gradient, the distance of the field-relevant conductors of a set of loops steadily decreases at least in the direction of the aperture of the V-shape of the gradient system. Alternatively or additionally, regarding the gradient coil for the Y-gradient, also the radius of a set of loops increases in X-direction to the aperture of the V-shape with the outer conductors essentially remaining at the aperture.

A magnetic resonance imaging system according to an exemplary embodiment includes a power unit for applying a current to gradient coils, wherein the magnetic resonance imaging system is configured such that a group of gradient coils of the magnetic resonance imaging system for a similar gradient axis in different examination areas, wherein the gradient coils of the group are electrically connected in a series and/or parallel connection, and the group being powered by the power unit.

In a gradient system according to an exemplary embodiment, comprises basic field magnets between adjacent examination areas, wherein a single gradient coil for a gradient axis is connected with a group of basic field magnets.

An X-gradient field according to an exemplary embodiment has a toroidal shape over the examination areas. An X-gradient field according to an exemplary embodiment has a bipolar distribution with a positive component (added to and increasing the basic magnetic field B0) at positive X-values of the local X-coordinate and a negative component (subtracted from and decreasing the basic magnetic field B0) at negative X-values of local X-coordinate. For example, at negative X-coordinates, that is at spatial positions situated between the origin of the local coordinate system (e.g. the isocenter of an examination area) and the central axis of the MRI-scanner, the X-gradient field is negative and counteracting (is weakening) the static basic magnetic field B0. At positive X-coordinates, that is at spatial positions situated between the origin and the entrance of an examination area, the X-gradient field is positive, and it is adding to (is strengthening) the static basic magnetic field B0. In an exemplary embodiment, the global distribution of the X-gradient fields follow the same rules in all examination areas and are identical there (seen from the respective local coordinate system). In an exemplary embodiment, the gradient field lines close following a polygonal (e.g. hexagonal) contour over the imaging compartments. At inner spatial positions (x<0) the polygonal and closed constant field lines run in opposite direction to B0, whilst at outer spatial positions (x>0) the gradient field lines run with the B0 lines. For the ideal gradient distribution, the resulting magnetic field at any spatial position in the local coordinate system is given by the expression: $B(x,y,z)=B0+Gx{\times}x$, where Gx is the selected strength of the X-gradient controlled by the intensity of the current flowing into the gradient coils.

All the inventive features disclosed above for the X-gradient system apply for the Y-gradient field as well, with the single difference that the Y-gradient field is implemented along the vertical Y-axis instead along the horizontal X-axis. Therefore, in an exemplary embodiment, the Y-gradient fields are also toroidally or polygonally (e.g. hexagonally) closed over and throughout all imaging compartments. The Y-gradient field is strengthening the static basic magnetic field at those spatial regions where the local Y-coordinate is positive (y>0) and it is weakening the static basic magnetic field in those spatial regions where the local Y-coordinate is negative (y<0). It should be noted that the direction of strengthening/weakening could also be the other way round.

Compared to the X-gradient system, the Y-gradient coils are equivalent to these X-gradient coils, wherein gradient currents and the associated wire patterns are rotated in plane by 90° in order to realize the target field distribution for the Y-gradient. For the ideal gradient distribution, the resulting magnetic field at any spatial position in the local coordinate system is given by the expression: $B(x,y,z)=B0+Gy{\times}y$, where Gy is the selected strength of the Y-gradient controlled by the intensity of the current flowing into the gradient coils.

Regarding the Z-gradient, in an exemplary embodiment, with reference to an examination area, the Z-gradient is weakening the static basic magnetic field B0 at those spatial regions where the local Z-coordinate is positive (z>0) and it is strengthening the static basic magnetic field B0 in those spatial regions where the local Z-coordinate is negative (z<0). For the ideal gradient distribution, the resulting magnetic field at any spatial position in the local coordinate system is given by the expression: $B(x,y,z)=B0-Gz{\times}z$ in any second examination area and $B(x,y,z)=B0+Gz{\times}z$, in any other second examination area, where Gz is the selected strength of the Z-gradient field controlled by the intensity of the current flowing into the gradient coils. Similar to the X and Y-gradients, the Z-gradient fields are also toroidally or polygonally (here hexagonally) closed over and throughout all examination areas.

It should be noted that there is a significant difference that avoids strong variations in magnetic field intensities at the boundary between two examination areas. In an exemplary embodiment (e.g. applying only to the Z-gradient system), the flow direction of the coil current alternates for every coil so that the (Z-)gradient fields are mirrored in adjacent examination areas.

In an exemplary embodiment, the coil current flows in counterclockwise direction in coils of any second examination area and in clockwise direction in any other second examination area (or the other way round). This is advantageous to generate the spatial distribution of the Z-gradient field within an imaging compartment and furthermore it is also allowing to use only six Z-gradient coils for all imaging compartments. The consequence of this solution is that the slope of the resulting Z-gradient field alternates every imaging compartment.

It should be noted that at the boundaries between two adjacent imaging regions the intensity of the magnetic field doesn't change abruptly but it is passing continuously from one region into the next one. For example, within the right-hand half on the first examination area as the local Z-coordinate (z<0) approaches the peak negative value the static basic magnetic field increases according to the expression $B(z)=B0-Gz{\times}z$ and it reaches the maximum amplitude at the boundary to the first examination area. Within the left-hand half on the second examination area, where the local Z-coordinate (z>0) the static basic magnetic field decreases following the expression $B(z)=B0+Gz{\times}z$ and it reaches zero amplitude in the middle of the second examination area when z=0.

With reference now to the second examination area, the Z-gradient is strengthening the static basic magnetic field at those spatial regions where the local Z-coordinate is positive (z>0) and it is weakening the static basic magnetic field B0 in those spatial regions where the local Z-coordinate is negative (z<0). For the ideal gradient distribution, the resulted magnetic field at any spatial position in the local coordinate system is given by the expression: $B(x,y,z)=B0+Gz{\times}z$, where Gz is the selected strength of the Z-gradient field controlled by the intensity of the current flowing into the gradient coils.

This inversion of the Z-gradient field will not significantly complicate the scan sequences running synchronously over all imaging compartments as it may be corrected by an coordinate transform from the logical gradient coordinate system to the physical gradient coordinate system inverting the Z-direction only for any second examination area.

In a gradient system according to an exemplary embodiment, the, a gradient coil is formed by a plurality of loops of a conductor. In an exemplary embodiment, only one long conductor is wound into a number of loops, however, there could also appear open loops that are connected to another. In the following, the loops of a coil are designated as a "set of loops", wherein any references to moving actions are meant to be understood as changes of following loops. Designs according to exemplary embodiments are provided below (alternatively or additionally):

The loops of a gradient coil for the X-gradient comprising two sets of contra-rotating loops adjacent in X-direction, wherein the radius of a set of loops increases, with the outer conductors in X-direction (the front and the back side) essentially remaining at the sides of the gradient coil. This means that the shape of such coil reminds one of a butterfly The loops of a gradient coil for the Y-gradient comprising two sets of contra-rotating loops adjacent in Y-direction, wherein the radius of a set of loops increases, with the outer conductors in Y-direction essentially remaining at the sides of the gradient coil (the sides perpendicular to the front and the back side). This means that the coil may look as the coil for the X gradient only rotated 90°.

The loops of a gradient coil for the Z-gradient comprising a set of increasing loops, wherein the center of the loops essentially remain in the center of the gradient coil. This means that the coils may be coaxial but growing bigger, at least in X-direction.

In the following, designs of coils according to exemplary embodiments are described. These designs result in linear gradient fields that increase in the direction of the mouth of the V-shape (to the front side) of the gradient system to compensate for the radial effect.

Regarding the gradient coil for the X-gradient, the distance of the field-relevant conductors of a set of loops steadily decreases at least in the direction of the aperture of the V-shape (in direction to the front side) of the gradient system. The field relevant conductors are these part of the loops that determine the magnetic field of a gradient.

Regarding the gradient coil for the Z-gradient, the distance of the field-relevant conductors of a set of loops steadily decreases at least in the direction of the aperture of the V-shape (in direction to the front side) of the gradient system.

Regarding the gradient coil for the Y-gradient, the radius of a set of loops increases in X-direction as well as in Y-direction with the outer conductors at the aperture of the V-shape essentially remaining at the side of the aperture (i.e. at the front side) as well as at the sides perpendicular to the front side.

Various hardware or software tools can be used to further fine-tune these wire patterns in order to meet some additional constrains such as the gradient linearity, to reduce the stray fields, the amplitude of mechanical vibrations and the level of acoustic noise or peripheral nerve stimulation.

The described wire pattern distributions could eliminate the inherent non-linearity of the gradient fields along a radial direction or along the local X-axis. This non-linearity only results with V-shaped gradient coils when the wire pattern density along the X-axis is approximately constant.

Special loop-shaping as described above may eliminate non-linear components along the X-axis for the X and the Z gradient coils by modifying the wire spacing along the X-axis from a constant one to a more quadratic one, with the wire density increasing approximatively quadratically with the radial distance to the axis of symmetry (e.g. of a toroid basic magnet). For the Y gradient coils an exemplary solution adds an additional wire distribution having constant spacing along the X-axis. This is similar to the wire patterns for the magnet coil used for generating the static basic magnetic field B0.

In a magnetic resonance imaging system according to an exemplary embodiment, the gradient system comprises a number of gradient coils covering a side (or at least a part of a side) of a whole field-of-view of an examination area, which may be mechanically and/or permanently attached to the MRI-scanner of the magnetic resonance imaging system.

In a magnetic resonance imaging system according to an exemplary embodiment, central planes of gradient coils of the gradient system on at least one side of the examination area are arranged parallel to basic field magnetic coils of a MRI-scanner of the magnetic resonance imaging system. Thus, the MRI-scanner has inclined basic field magnets and the gradient system follows the arrangement of the basic field magnets.

In an exemplary embodiment, the opening angle of the V-shape of the gradient system is 120° (e.g. for a star shaped MRI scanner with 3 examination areas), 90° (e.g. for a star shaped MRI scanner with 4 examination areas), 60° (e.g. for a star shaped MRI scanner with 6 examination areas) or 45° (e.g. for a star shaped MRI scanner with 8 examination areas).

The advantage of a gradient system according to the disclosure is that a (toroidal) parallel MRI-scanner with global gradient coils operating synchronously in all examination areas can be realized to generate global gradient fields, especially having a toroidal distribution. One special advantage of this solution is that it only needs a minimum of three gradient power amplifiers (GPAs) for all examination regions, whilst the costs and fitting space for the gradient coils are further reduced. Moreover, concerning the toroidal arrangement, there will be no stray gradient fields leaking from one imaging region into the others as all gradient coils operate together and in conjunction and all contribute to the same toroidally distributed global gradient fields.

FIG. 1 shows a schematic representation of a magnetic resonance imaging (MRI) system 1 according to an exemplary embodiment. The MRI system 1 includes magnetic resonance scanner (data acquisition unit) 2 with an examination space 3 or patient tunnel in which a patient or test person is positioned on a driven bed 8, in whose body the actual examination object O is located.

In an exemplary embodiment, the magnetic resonance scanner 2 is equipped with a basic field magnet system 4, a gradient system 6, radio-frequency (RF) transmission antenna system 5, and an RF reception antenna system 7. In the shown exemplary embodiment, the RF transmission antenna system 5 is a whole-body coil permanently installed in the magnetic resonance scanner 2, in contrast to which the RF reception antenna system 7 is formed as local coils (symbolized here by only a single local coil) to be arranged on the patient or test subject. In principle, however, the whole-body coil can also be used as an RF reception antenna system, and the local coils can respectively be switched into different operating modes.

The basic field magnet system is designed in a typical manner so that it generates a basic magnetic field in the longitudinal direction of the patient, i.e. along the longitudinal axis of the magnetic resonance scanner 2 that proceeds in the z-direction. The gradient system 6 typically includes individually controllable gradient coils in order to be able to switch (activate) gradients in the X-direction, y-direction or z-direction independently of one another.

The MRI system 1 shown here is a whole-body system with a patient tunnel into which a patient can be completely introduced. However, in principle the disclosure can also be used at other MRI systems, for example with a laterally open, C-shaped housing, as well as in smaller magnetic resonance scanners in which only one body part can be positioned.

Furthermore, the MRI system 1 has a central controller 13 that is used to control the MRI system 1. This central controller 13 includes a sequence controller 14 for measurement sequence control. With this sequence controller 14, the series of radio-frequency pulses (RF pulses) and gradient pulses can be controlled depending on a selected pulse sequence. In an exemplary embodiment, the controller 13 includes processor circuitry that is configured to perform one or more functions and/or operations of the controller 13, including controlling the MRI system 1.

To output the individual RF pulses of a pulse sequence, the central controller 13 has a radio-frequency transmitter 15 that generates and amplifies the RF pulses and feeds them into the RF transmission antenna system 5 via a suitable interface (not shown in detail). To control the gradient coils of the gradient system 6, the controller 13 has a gradient system interface 16. The sequence controller 14 communicates in a suitable manner with the radio-frequency transmitter 15 and the gradient system interface 16 to emit the pulse sequence.

Moreover, the controller 13 has a radio-frequency receiver 17 (likewise communicating with the sequence controller 14 in a suitable manner) in order to acquire magnetic resonance signals (i.e. raw data) for the individual measurements, which magnetic resonance signals are received in a coordinated manner from the RF reception antenna system 7 within the scope of the pulse sequence.

A reconstructor 18 receives the acquired raw data and reconstructs magnetic resonance image data therefrom for the measurements. This reconstruction is typically performed on the basis of parameters that may be specified in the respective measurement or control protocol. For example, the image data can then be stored in a memory 19.

Operation of the central controller 13 can take place via a terminal 10 with an input unit and a display unit 9, via which the entire MRI system 1 can thus also be operated by an operator. MR images can also be displayed at the display unit 9, and measurements can be planned and started by means of the input unit (possibly in combination with the display unit 9), and in particular suitable control protocols can be selected (and possibly modified) with suitable series of pulse sequence PS as explained above.

The MRI system 1 according to the disclosure, and in particular the controller 13, can have a number of additional components that are not shown in detail but are typically present at such systems, for example a network interface in order to connect the entire system with a network and be able to exchange raw data and/or image data or, respectively, parameter maps, but also additional data (for example patient-relevant data or control protocols).

The manner by which suitable raw data are acquired by radiation of RF pulses and the generation of gradient fields, and MR images are reconstructed from the raw data, is known to those skilled in the art and thus need not be explained in detail herein.

Figure 2:
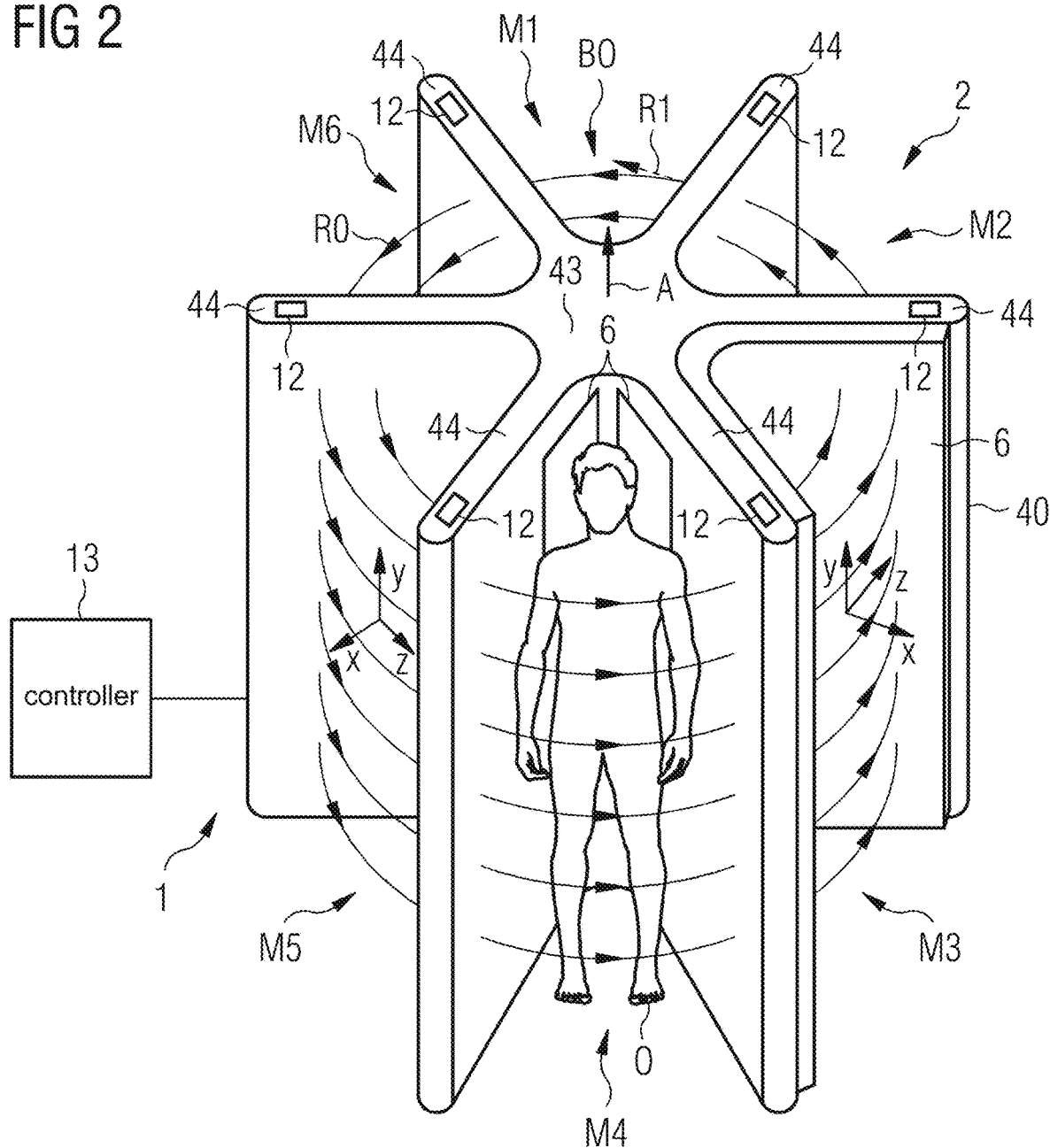
FIG. 2 shows a magnetic resonance tomography system, according to an exemplary embodiment of the disclosure, with a star-shaped basic field magnet arrangement with circular closed basic magnetic field lines.

FIG. 2 shows an exemplary embodiment of a magnetic resonance tomography system 1 with a star-shaped basic field magnet arrangement 40. The MRI-system comprises a toroidal MRI scanner 2 that allows scanning up to six patients O simultaneously.

Shown here is a magnetic resonance scanner 2, the function of which can be controlled by a controller 13. The controller 13 can in principle be constructed in a similar manner and have the same components as the controller 13 in a conventional MR system according to FIG. 1. Likewise, it can also have a suitable terminal or the like (which is not shown here).

The basic field magnet arrangement 40 of the magnetic resonance scanner 2 in this figure comprises six (here identical) basic field magnet segments 44, which in this embodiment are arranged in a star shape about a central axis A with a rotational symmetry of 60°. The basic magnetic field B0 indicated by arrows has a basic field main direction R0, which runs in the form of a circle or a toroidal magnetic field.

This magnet solution provides six examination areas (imaging volumes) M1, M2, M3, M4, M5, M6, wherein the homogeneity of the magnet field B0 is high enough for conducting MR imaging sequences as known from prior art of MRI. Hence, this scanner is supposed to acquire raw data and to reconstruct images acquisition sequences and image reconstruction methods well-known in the art (e.g. FIG. 1).

For each examination area M1, M2, M3, M4, M5, M6 there is a local coordinate system XYZ associated therewith as exemplary depicted for two examination areas M3, M5. The local Z-axis is running parallel to and pointing in the same direction with the static basic magnetic field B0. The Y-axis is parallel to the vertical rotational symmetry axis (central axis A) of the MRI-scanner 2, while the X-axis corresponds to the radial direction pointing from the center of symmetry outwards from the magnet through the vertical midplane of the imaging compartment.

Figure 3:
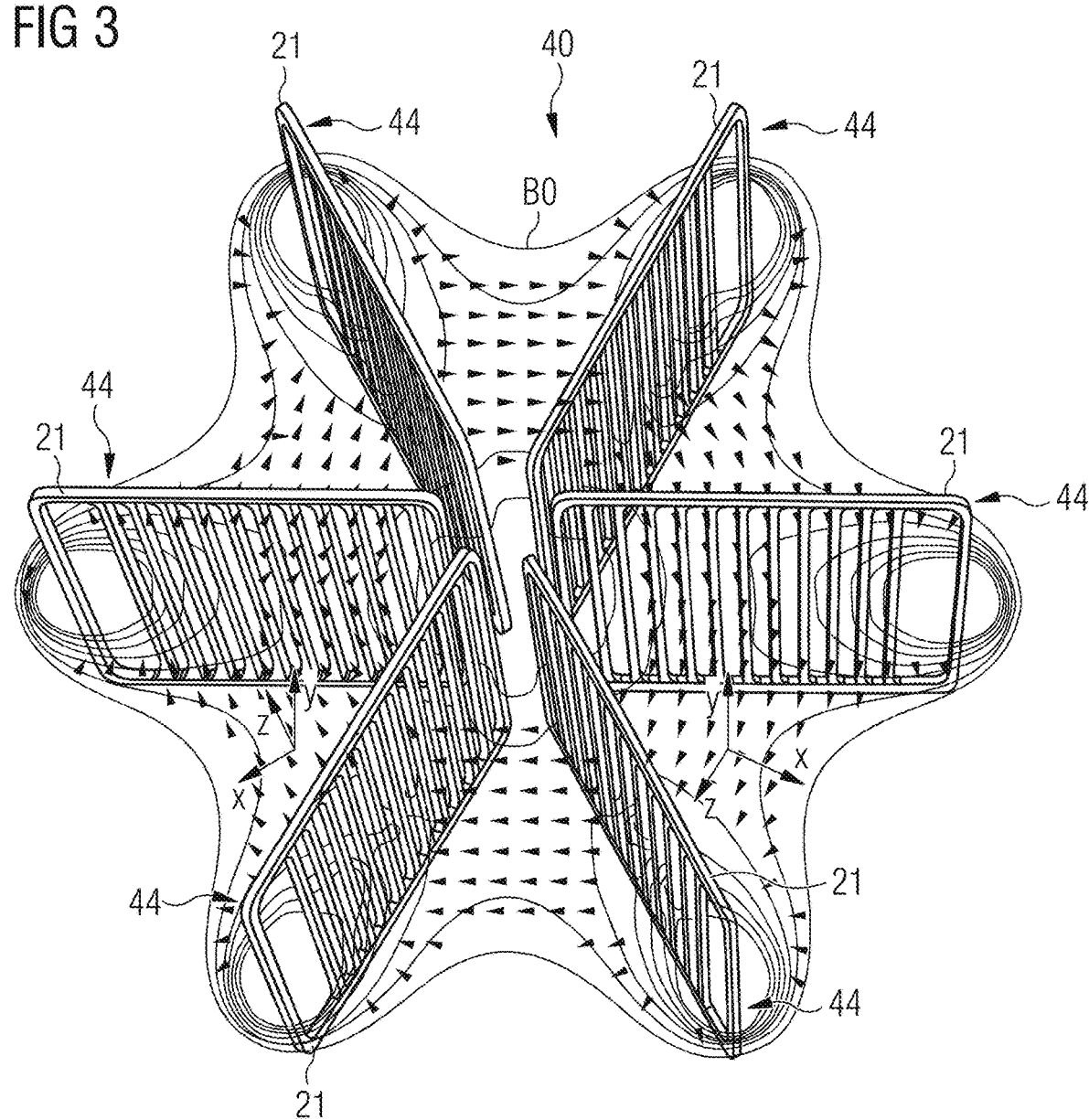
FIG. 3 shows a schematic representation of the individual basic field magnet segments of a star-shaped basic field magnet arrangement with polygonal closed basic magnetic field lines according to an exemplary embodiment of the disclosure.

FIG. 3 shows a detailed schematic representation of the individual basic field magnet segments 44 of a star-shaped basic field magnet arrangement 40. Six coil-arrangements can be seen here as basic field magnet segments 44 of the basic field magnet arrangement 40.

It should be noted that in FIG. 3 the lines of the basic magnetic field B0 doesn't form circles, but hexagonal contours in each examination area M1, M2, M3, M4, M5, M6. The field lines of the basic magnetic field B0 form parallel lines.

This "six-pack" toroidal MRI-scanner allows scanning up to six patients simultaneously in six imaging volumes (examination areas) wherein the homogeneity of the magnet field B0 is high enough for conducting MR imaging sequences as known from prior art. This scanner is supposed to acquire raw data and to reconstruct MR images by acquisition and image reconstruction methods as explained in the course of FIG. 1.

As already indicated in FIG. 2, for each imaging volume there is a local coordinate system XYZ associated therewith as exemplary depicted here only for two imaging volumes. Again, the local Z-axis is running parallel to and pointing in the same direction with the static basic magnetic field B0. The Y-axis is parallel to the rotational symmetry axis of the six-pack magnet system, while the X-axis corresponds to the radial direction pointing from the center of symmetry outwards from the magnet.

Arrows and iso-lines depict the overall distribution of the static basic magnetic field B0 within a cross sectional planar cut through the middle of the magnet. The local magnetic field vectors depicted by small arrows show the distribution of the local magnetic field magnitude (arrow size) and its direction (arrow orientation).

A significant advantage of such a symmetrical arrangement is the structural stability when the basic magnetic field B0 is switched on. The magnetic forces between the individual basic field magnetic segments 44 cancel each other out in the direction of the main magnetic field direction R0. Each basic field magnet segment 44 is attracted by its two neighbors, each with the same force. The resulting forces act inwardly towards the pillar 43 and can be compensated there very well by appropriate structural reinforcements.

Such a magnetic resonance imaging system 1 with a basic field magnet arrangement 40 according to FIGS. 2 and 3 permits measurements at six different examination areas M1, M2, M3, M4, M5, M6 (see FIG. 2), wherein in the illustrated example a measurement of an object O (a patient as shown or an inanimate object) occurs at examination area M4, wherein a patient stands here upright on vertical walls of the basic field magnet arrangement 40. Theoretically, measurements could take place simultaneously at all six examination areas M1, M2, M3, M4, M5, M6. A central pillar 43 holds the basic field magnet segments 44 in place and may also comprise technical components, such as e.g. the electrical connections or even the power supply.

In each case, measuring devices 12 (only shown symbolically) or the components respectively required for this purpose at examination area M1, M2, M3, M4, M5, M6, such as an HF coil, can be located at examination areas M1, M2, M3, M4, M5, M6 Transmitting coil of an RF transmission system, an RF reception coil of an RF reception system and/or a common RF transmission/reception coil. Likewise, this may include gradient and/or shim coils. All of these components can be controlled coordinated by the common controller 13.

Of course, a magnetic resonance scanner 2 may also have more than six examination areas M1, M2, M3, M4, M5, M6, its height may be lower, or it may be designed for examining small areas of the body, e.g. for head examinations or examinations of the extremities, the female breast, the prostate, the liver, kidneys or other organs. The star-shaped basic field magnet arrangement 40 could also be positioned lying.

In FIG. 2 an example for a local gradient system 6 is shown in one examination area M4 around the head of the patient. The V-shape of the gradient system 6 follows the angle between two basic field magnet segments 44, i.e. 60°.

Another example for a gradient system 6 is shown, also in FIG. 2, in an adjacent examination area M3. This gradient system 6 comprises large gradient coils that covers the whole field-of-view of the examination area M3 and is mechanically and permanently attached to the basic field magnet segments 44 of the MRI scanner 2. Each examination area M1, M2, M3, M4, M5, M6 may have such a V-shaped gradient system 6 attached thereto and consisting in two blocks: the right-block and the mirrored paired left-block. The V-shaped architecture of gradient systems 6 makes better use of the magnetic field space available within the examination regions that is shaped like a triangular or trapezoidal prism. As for the local gradient system 6, each block consists of a stack of planar gradient coils 25x, 25y, 25z (see following figures), e.g. each block integrates one half of the X, Y and Z gradient coil pairs. Furthermore, the blocks could also integrate magnetic field shim coils and/or active shielding coils so configured to attenuate the stray gradient fields outside the imaging volume that would otherwise penetrate the adjacent examination regions and/or imaging volumes. The gradient system 6 may further include dedicated gradient power amplifiers for each axis GPAx, GPAy and GPAz and for each examination region, preferably all being controlled by a common central unit.

In the following, the principle of the disclosure is shown in a few examples. It should be noted that in these examples for the gradient system, the same reference sign is used as for the gradient systems mentioned before. The reason is that the intent and purpose of the gradient systems 6 is always the same, i.e. producing a suitable gradient field for measurements. A gradient system 6 according to the disclosure can absolutely use the designs as described above, wherein however gradient coil arrangements should be installed in most (all) examination areas M1, M2, M3, M4, M5, M6. It would be advantageous to use identical or at least similar gradient coil arrangements in the examination areas M1, M2, M3, M4, M5, M6, since this would result in a periodic gradient field. The difference of gradient systems 6 of the state of the art and a gradient system 6 according to the disclosure is the functional arrangement (e. g. the internal wiring) of the coils 25a, 25b 25c so that coils in different examination areas M1, M2, M3, M4, M5, M6 can be driven in a synchronous manner. This is explained in the following.

Figure 4:
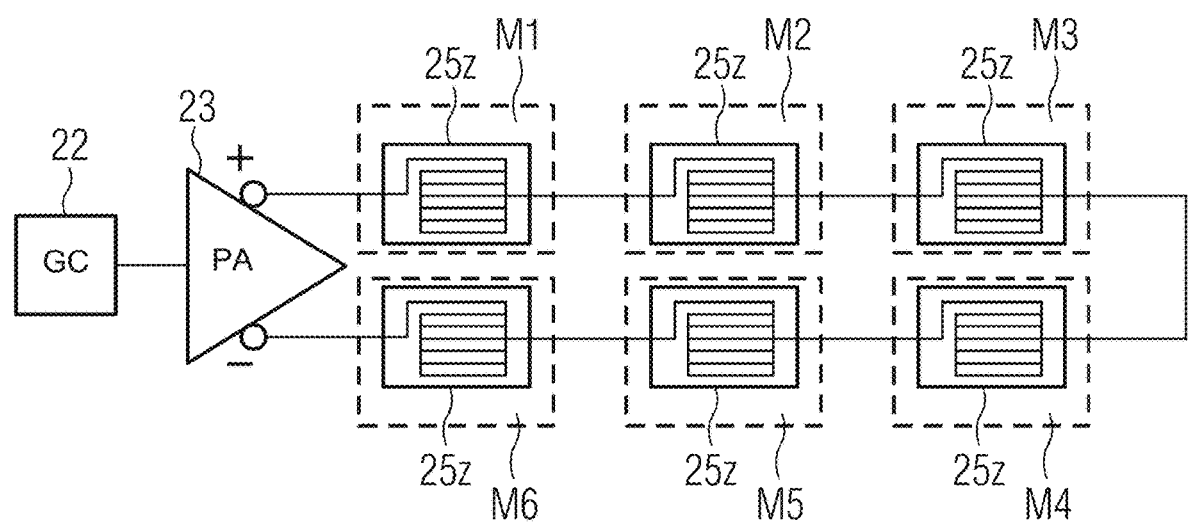
FIG. 4 shows a configuration of gradient coils driven by a single gradient power amplifier according to an exemplary embodiment of the disclosure.

FIG. 4 shows a configuration of Z-gradient coils 25z driven by a single gradient power unit 23 (e.g. power amplifier). The gradient coils 25z are in this example, the gradient coils 25z for the z-axis of a gradient system 6 for a six-pack parallel MRI-scanner 2 (s. e.g. FIG. 2), wherein the gradient controller 22 of the gradient system 6 provides a gradient signal for one single gradient power amplifier ("GPA") for the gradient coils 25z of the z-axis. Since in this example the MRI-scanner 2 comprises only one gradient coil 25z per examination area M1, M2, M3, M4, M5, M6, the GPA drives a total of six gradient coils per axis, each one of the gradient coils being singly hosted within one examination area M1, M2, M3, M4, M5, M6. In FIG. 2, where there are pairs of gradient coils shown, the number of gradient coils 25z being driven by one single GPA would be 12.

Figure 5:
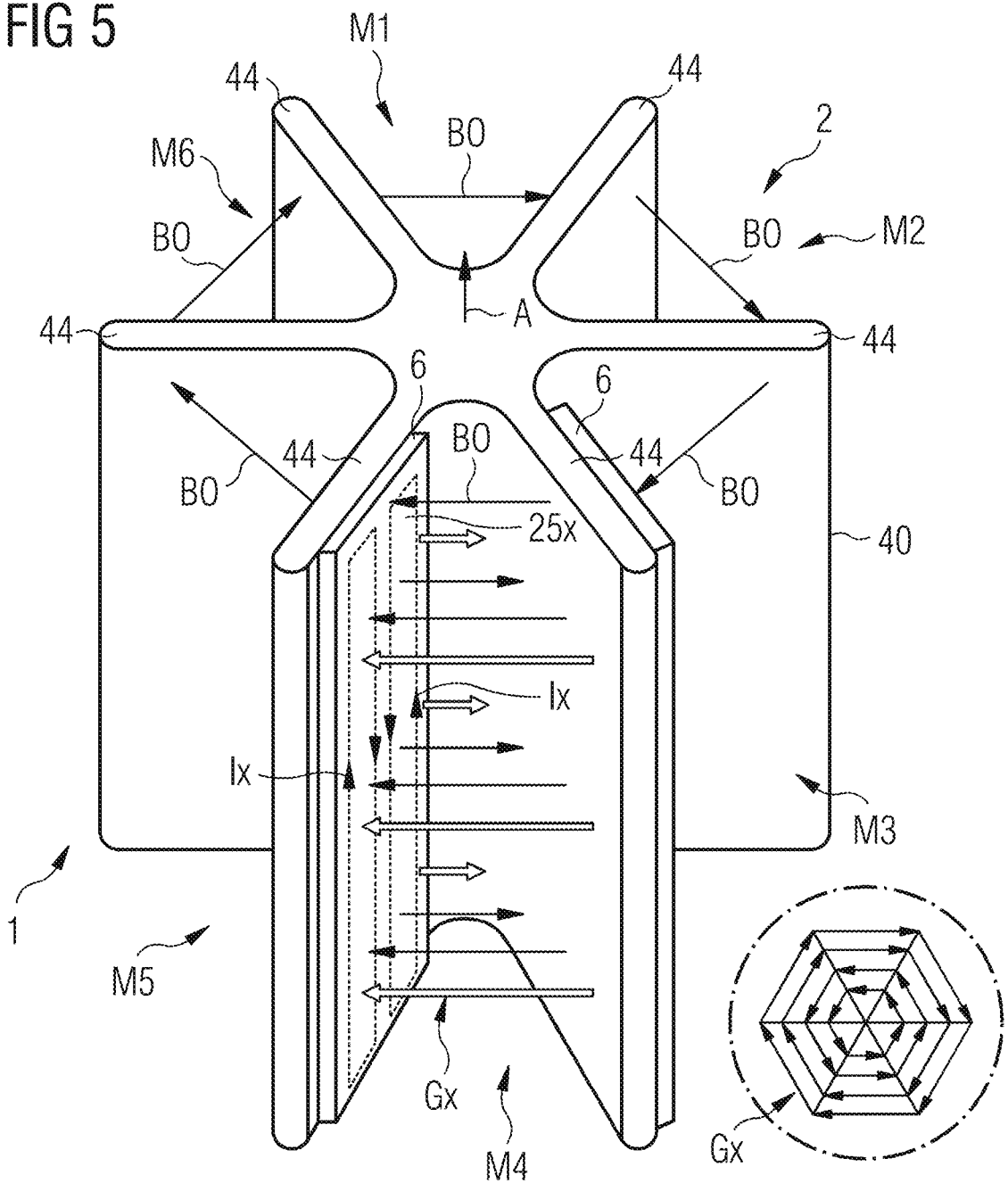
FIG. 5 shows an exemplary X-gradient field according to an exemplary embodiment of the disclosure.

FIG. 5 shows an exemplary X-gradient field Gx. The figure shows the target spatial distribution of the global gradient field Gx for the X-axis in on examination area M4, however as depicted in the top view at the bottom right of the figure, it surely should extend over all six examination areas M1, M2, M3, M4, M5, M6. The gradient field has a bipolar distribution with a positive component (added to and increasing the basic magnetic field B0) at positive X-values of the local X-coordinate and a negative component (subtracted from and decreasing the basic magnetic field B0) at negative X-values of local X-coordinate. This distribution is exemplary depicted in examination area M4 by arrows, which thickness indicates the field strength of the X-gradient field Gx. A thicker arrow symbolizes a stronger local gradient strength.

The arrows point into the direction of the local gradient field. At negative X-coordinates, that is at spatial positions situated between the origin of the local coordinate system (e.g. the isocenter of an examination area M1, M2, M3, M4, M5, M6) and the central axis A of the MRI-scanner 2, the X-gradient field Gx is negative and counteracting (is weakening) the static basic magnetic field B0. At positive X-coordinates, that is at spatial positions situated between the origin and the entrance of an examination area M1, M2, M3, M4, M5, M6, the X-gradient field Gx is positive, and it is adding to (is strengthening) the static basic magnetic field B0. The global distribution of the X-gradient fields Gx preferably follows the same rules in all examination areas M1, M2, M3, M4, M5, M6 and is preferably identical there (seen from the respective local coordinate system). As depicted in the top view at the bottom right, the gradient field lines close following a hexagonal contour over the imaging compartments. At inner spatial positions (x<0) the polygonal and closed constant field lines run in opposite direction to B0, whilst at outer spatial positions (x>0) the gradient field lines run with the B0 lines.

Only for two examination areas M4, M5 the figure also exemplarily depicts the gradient coils 25x and the main gradient current patterns used to generate this spatial distribution of X-gradient fields. In this configuration the pair of current loops generate the toroidally distributed positive X-gradient fields Gx, wherein field vectors depicted by arrows pointing from the right side to the left side. It should be noted that the pair of current loops belong to a single gradient coil 25x.

The pair of current loops generate the toroidally distributed negative X-gradient fields, wherein again field vectors depicted by arrows pointing from the left side to the right side. This wire and current patterns repeat identically for all other X-gradient coils 25x (see picture at the bottom right). All X-gradient coils 25x work together in conjunction to generate the X-gradient fields having the toroidal distribution depicted by the figure.

It should be noted that FIG. 5 depicts a simplified, more like an ideal spatial distribution of the gradient fields. In reality the gradient fields are non-linear across the imaging compartment and far away from a central/symmetry axis. Moreover, the so-called concomitant terms occur as reinforced by the laws of physics. Whenever a linear gradient is activated, concomitant magnetic fields with non-linear spatial dependence result occur. This is a consequence of Maxwell's equations, i.e. within the imaging volume the magnetic field must have zero divergence and has negligible curl.

FIG. 6 shows the distribution of the Y-gradient field Gy. All the inventive features disclosed above for the X-gradient system and depicted by FIG. 5 apply for the Y-gradient field Gy as well, with the single difference that the Y-gradient field Gy is implemented along the vertical Y-axis instead along the horizontal X-axis. Therefore, in an exemplary embodiment, the Y-gradient fields Gy are also toroidally or polygonally (e.g. hexagonally) closed over and throughout all imaging compartments. The Y-gradient field Gy is strengthening the static basic magnetic field B0 at those spatial regions where the local Y-coordinate is positive (y>0) and it is weakening the static basic magnetic field B0 in those spatial regions where the local Y-coordinate is negative (y<0). It should be noted that the direction of strengthening/weakening could also be the other way round.

Like the X-gradient system, in an exemplary embodiment, there are six Y-gradient coils 25$y$ equivalent to the X-gradient coils 25$x$ in FIG. 5. The exemplary depicted gradient currents and the associated wire patterns are rotated in plane by 90° in order to realize the target field distribution for the Y-gradient field Gy.

Figure 7:
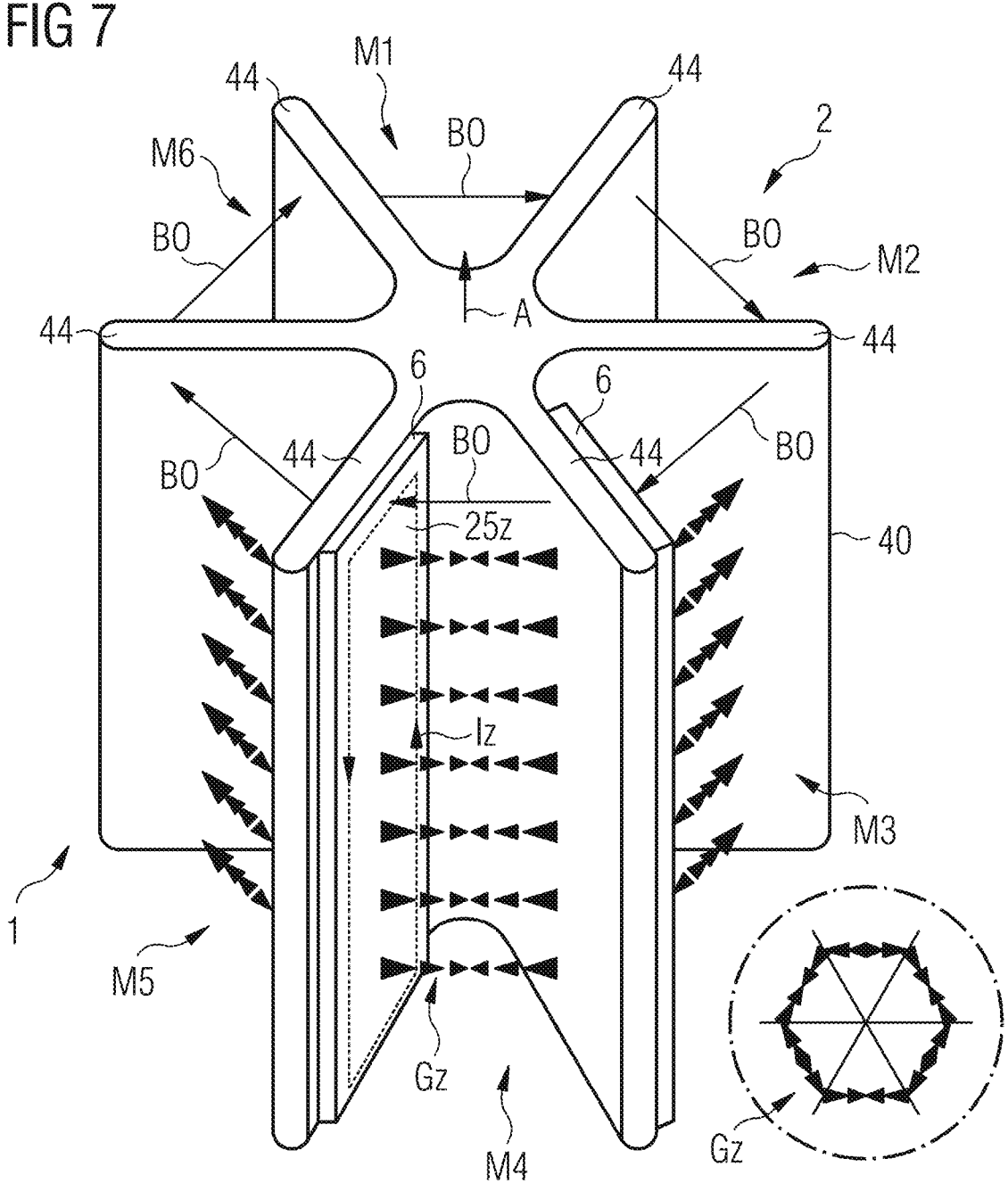
FIG. 7 shows an exemplary z-gradient field according to an exemplary embodiment of the disclosure.

FIG. 7 shows an exemplary Z-gradient field. This figure depicts the target magnetic field distribution resulted when the Z-gradient field Gz is active. In an exemplary embodiment, the Z-gradient system comprises six gradient coils 25$z$ with the corresponding wire patters and gradient currents. The Z-gradient field Gz is depicted only for three examination areas M3, M4, M5. However, as shown in the top view at the bottom right, they should be present in all examination areas M1, M2, M3, M4, M5, M6.

With reference to the examination area M4 at the front, the Z-gradient is weakening the static basic magnetic field B0 at those spatial regions where the local Z-coordinate is positive (z>0) and it is strengthening the static basic magnetic field B0 in those spatial regions where the local Z-coordinate is negative (z<0). Similar to the X and Y-gradients, the Z-gradient fields Gz are also toroidally or polygonally (here hexagonally) closed over and throughout all examination areas M1, M2, M3, M4, M5, M6.

It should be noted that there is a significant difference that avoids strong variations in magnetic field intensities at the boundary between two examination areas M1, M2, M3, M4, M5, M6. By a new and a further inventive approach (applying only to the Z-gradient system), the flow direction of the coil current alternates for every coil so that the Z-gradient fields are mirrored in adjacent examination areas M1, M2, M3, M4, M5, M6.

The coil current flows in counterclockwise direction in coils 25$z$ of any second examination area M1, M3, M5 and in clockwise direction in any other second examination area M2, M4, M6 (or the other way round). This is advantageous to generate the spatial distribution of the Z-gradient field within an imaging compartment and furthermore it is also allowing to use only six Z-gradient coils for all imaging compartments. The consequence of this solution is that the slope of the Z-gradient field alternates every imaging compartment as further depicted by FIG. 8.

This FIG. 8 clearly depicts the practical advantage of this inventive gradient system. It shows that at the boundaries between two adjacent imaging regions the intensity of the magnetic field doesn't change abruptly but it is passing continuously from one region into the next one. For example, within the right-hand half on the first examination area M1 as the local Z-coordinate (z<0) approaches the peak negative value the static basic magnetic field increases and it reaches the maximum amplitude at the boundary of the first examination area M1 to the second examination area M2. Within the left-hand half on the first examination area M1, where the local Z-coordinate (z>0) the static basic magnetic field decreases and it reaches zero amplitude in the middle of the first examination area M1 when z=0.

With reference now to the second examination area M2, the Z-gradient is strengthening the static basic magnetic field B0 at those spatial regions where the local Z-coordinate is positive (z>0) and it is weakening the static basic magnetic field B0 in those spatial regions where the local Z-coordinate is negative (z<0).

This inversion of the Z-gradient field Gz will not significantly complicate the scan sequences running synchronously over all imaging compartments as it may be corrected by a coordinate transform from the logical gradient coordinate system to the physical gradient coordinate system inverting the Z-direction only for any second examination area.

As the toroidal gradient field penetrates the magnet coils—these are the coils that generate the static basic magnetic field B0—it is a limitation of the solution requiring that the magnet coils need to tolerate the switching gradient fields without associated difficulties. For example, an electromagnet for low field MRI will have no problem with that requirement. A superconducting magnet will need special protection measures to reduce the amount of heat induced into e.g. Cu wires supporting the SC material. These magnets are e.g. known as "transparent" SC magnets.

Although the present disclosure has been disclosed in the form of preferred embodiments and variations thereon, it will be understood that numerous additional modifications and variations could be made thereto without departing from the scope of the disclosure. For the sake of clarity, it is to be understood that the use of "a" or "an" throughout this application does not exclude a plurality, and "comprising" does not exclude other steps or elements. The mention of a "unit" or a "device" does not preclude the use of more than one unit or device.

To enable those skilled in the art to better understand the solution of the present disclosure, the technical solution in the embodiments of the present disclosure is described clearly and completely below in conjunction with the drawings in the embodiments of the present disclosure. Obviously, the embodiments described are only some, not all, of the embodiments of the present disclosure. All other embodiments obtained by those skilled in the art on the basis of the embodiments in the present disclosure without any creative effort should fall within the scope of protection of the present disclosure.

It should be noted that the terms "first", "second", etc. in the description, claims and abovementioned drawings of the present disclosure are used to distinguish between similar objects, but not necessarily used to describe a specific order or sequence. It should be understood that data used in this way can be interchanged as appropriate so that the embodiments of the present disclosure described here can be implemented in an order other than those shown or described here. In addition, the terms "comprise" and "have" and any variants thereof are intended to cover non-exclusive inclusion. For example, a process, method, system, product or equipment comprising a series of steps or modules or units is not necessarily limited to those steps or modules or units which are clearly listed, but may comprise other steps or modules or units which are not clearly listed or are intrinsic to such processes, methods, products or equipment.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

For the purposes of this discussion, the term "processor circuitry" shall be understood to be circuit(s), processor(s), logic, or a combination thereof. A circuit includes an analog circuit, a digital circuit, state machine logic, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A gradient system for a magnetic resonance imaging system comprising:
   at least two examination areas using a common basic magnetic field and a number of gradient coils in the at least two examination areas, and
   a gradient controller configured to control electric current flowing through at least two gradient coils, for similar gradient axes in different examination areas, in a temporal synchronous manner, wherein each of the at least two gradient coils comprise a central plane, the at least two gradient coils being arranged such that the respective central planes of the at least two adjacent gradient coils are at an angle greater than 10° to another so that the at least two gradient coils form a V-shaped arrangement.

2. The gradient system according to claim 1, comprising a group of gradient coils for a similar gradient axis in different examination areas, the gradient coils of the group being electrically connected in a series and/or parallel, the group of gradient coils being powered by a single power unit, wherein the gradient coils for a similar gradient axis in all examination areas are powered by one single power unit.

3. The gradient system according to claim 1, wherein the gradient coils are arranged such that a resulting gradient field has a toroidal shape or a toroidal shape with straight passages, the gradient coils being arranged star-shaped around at least one central axis, rotary-symmetrical.

4. The gradient system according to claim 1, wherein:
   gradient coils are arranged such that an examination area of the at least two examination areas comprises a gradient coil on only a single side of the examination area,
   the number of gradient coils for a group of the examination areas corresponds to a number of examination areas in the group of examination areas, and
   a separating element between adjacent examination areas of the at least two examination areas comprises only a single gradient coil for each gradient axis for both of the adjacent examination areas.

5. The gradient system according to claim 1, wherein the gradient coils are bi-planar gradient coils, wherein a number of gradient coils is formed to cover a side of a whole field-of-view of an examination area, the gradient coils being mechanically and/or permanently attachable to an MRI-scanner.

6. The gradient system according to claim 1, comprising magnetic field shim coils and/or active shielding coils, wherein central planes of the magnetic field shim coils and/or the active shielding coils are respectively arranged parallel to the central planes of the at least two gradient coils.

7. The gradient system according to claim 1, wherein the gradient coils for a gradient of a Z-axis are connected to the gradient controller such that adjacent gradient coils are configured to apply a mirrored magnetic field, the Z-axis running parallel to the common basic magnetic field.

8. A controller for a magnetic resonance imaging system, comprising:
   an interface configured to interface with a scanner of the magnetic resonance imaging system, wherein the magnetic resonance imaging system further includes: at least two examination areas, a basic field magnet configured to generate a common basic magnetic field, and a gradient system including gradient coils in each examination area of the at least two examination areas; and
   a processor configured to control, in a temporal synchronous manner, an application of electric current flowing through the at least two gradient coils for similar gradient axes in different examination areas of the at least two examination areas, wherein a number of the at least two gradient coils cover a side of a whole field-of-view of an examination area of the at least two examination areas, the number of the at least two gradient coils are mechanically and/or permanently attached to the scanner.

9. A magnetic resonance imaging system comprising:
at least two examination areas;
a basic field magnet configured to generate a common basic magnetic field; and
a gradient system including:
gradient coils in each examination area of the at least two examination areas, and
a gradient controller configured to control electric current flowing through at least two of the gradient coils, for similar gradient axes in different examination areas, in a temporal synchronous manner, wherein central planes of the gradient coils of the gradient system on at least one side of an examination area, of the at least two examination areas, are parallel to the basic field magnet.

10. The magnetic resonance imaging system according to claim 9, further comprising a power unit configured to apply a current to the gradient coils, wherein the magnetic resonance imaging system comprises a group of gradient coils for a similar gradient axis in the different examination areas, wherein the gradient coils of the group are electrically connected in a series and/or parallel, the group of gradient coils being powered by the power unit.

11. The magnetic resonance imaging system according to claim 9, wherein the basic field magnet is located between adjacent examination areas of the at least two examination areas, a single gradient coil for a gradient axis being connected with a group of basic field magnets.

12. The magnetic resonance imaging system according to claim 9, wherein the gradient system comprises a number of gradient coils covering a side of a whole field-of-view of an examination area, the number of gradient coils being mechanically and/or permanently attached to an MRI-scanner of the magnetic resonance imaging system.

13. A gradient system for a magnetic resonance imaging system comprising:
at least two examination areas using a common basic magnetic field and a number of gradient coils in the at least two examination areas, and
a gradient controller configured to control electric current flowing through at least two gradient coils, for similar gradient axes in different examination areas, in a temporal synchronous manner, wherein the at least two gradient coils are arranged such that a resulting gradient field has a toroidal shape or a toroidal shape with straight passages, the at least two gradient coils being arranged star-shaped around at least one central axis, rotary-symmetrical.

14. A gradient system for a magnetic resonance imaging system comprising:
at least two examination areas using a common basic magnetic field and a number of gradient coils in the at least two examination areas, and
a gradient controller configured to control electric current flowing through at least two gradient coils, for similar gradient axes in different examination areas, in a temporal synchronous manner, wherein:
gradient coils are arranged such that an examination area of the at least two examination areas comprises a gradient coil on only a single side of the examination area,
the number of gradient coils for a group of the examination areas corresponds to a number of examination areas in the group of examination areas, and
a separating element between adjacent examination areas of the at least two examination areas comprises only a single gradient coil for each gradient axis for both of the adjacent examination areas.

* * * * *